US011039749B1

(12) United States Patent
Al-Helali et al.

(10) Patent No.: US 11,039,749 B1
(45) Date of Patent: Jun. 22, 2021

(54) TWO FACTOR AUTHENTICATION USING MOLECULAR COMMUNICATION—A SYSTEM AND METHOD

(71) Applicants: Alfaisal University, Riyadh (SA); AbdulAziz Al-Helali, Toronto (CA); Ben Liang, Toronto (CA)

(72) Inventors: AbdulAziz Al-Helali, Toronto (CA); Ben Liang, Toronto (CA); Nidal Nasser, Riyadh (SA)

(73) Assignee: Alfaisal University, Riyadh (SA)

( * ) Notice: Subject to any disclaimer, the term of this patent is extended or adjusted under 35 U.S.C. 154(b) by 0 days.

(21) Appl. No.: 16/852,753

(22) Filed: Apr. 20, 2020

Related U.S. Application Data

(63) Continuation-in-part of application No. 16/720,908, filed on Dec. 19, 2019.

(51) Int. Cl.
*A61B 5/00* (2006.01)
*A61N 1/372* (2006.01)
*H04W 12/06* (2021.01)
*H04B 13/00* (2006.01)

(52) U.S. Cl.
CPC ........ *A61B 5/0028* (2013.01); *A61N 1/37254* (2017.08); *H04B 13/005* (2013.01); *H04W 12/06* (2013.01); *H04L 2463/082* (2013.01)

(58) Field of Classification Search
CPC ............. A61N 1/37254; H04W 12/06; H04W 12/1204; H04L 63/083; H04L 2463/082; H04B 13/005; A61B 5/0028
See application file for complete search history.

(56) References Cited

U.S. PATENT DOCUMENTS

| | | | |
|---|---|---|---|
| 8,886,316 B1* | 11/2014 | Juels | H04W 12/003 607/31 |
| 10,734,119 B2* | 8/2020 | Kozloski | H04W 12/06 |
| 2006/0064587 A1* | 3/2006 | Braverman | H04L 9/0662 713/168 |
| 2008/0280342 A1* | 11/2008 | Hiyama | H04B 13/00 435/174 |
| 2010/0238955 A1* | 9/2010 | Sung | H04B 13/005 370/498 |
| 2016/0250490 A1* | 9/2016 | Hoffman | A61N 1/37254 607/60 |
| 2017/0312530 A1* | 11/2017 | Schilling | H04L 67/12 |
| 2018/0236169 A1* | 8/2018 | Zhang | A61M 39/20 |
| 2018/0241481 A1* | 8/2018 | Das | H04B 10/90 |
| 2020/0188708 A1* | 6/2020 | Myslinski | A61K 8/26 |

* cited by examiner

*Primary Examiner* — Catherine M Voorhees
(74) *Attorney, Agent, or Firm* — Ellenoff Grossman & Schole LLP; James M. Smedley; Alex Korona

(57) ABSTRACT

Disclosed herein is a Two Factor Authentication system using Molecular Communication (TFAMoCo) to prevent hacking the wireless link of an IEMD. Also, disclosed herein a Two Factor Authentication using Molecular Communication (TFAMoCo) method that wakes up an IEMD and activate its electromagnetic (EM) module utilizing the IEMD's molecular communication (MC) module for detecting a molecular signal that carries a PIN number.

15 Claims, 7 Drawing Sheets

TWO FACTOR AUTHENTICATION USING MOLECULAR COMMUNICATION—A SYSTEM AND METHOD

CROSS REFERENCE TO RELATED APPLICATION

The instant application is a continuation in part of U.S. application Ser. No. 16/720,908 filed on 19 Dec. 2019. The pending U.S. application Ser. No. 16/720,908 is hereby incorporated by reference in its entireties for all of its teachings.

FIELD OF INVENTION

The present invention relates generally to implanted electronic medical devices (IEMDs), and more specifically, to securing the wireless communication link with an implanted electronic medical device. In addition, the invention relates to using molecular communication in the human body.

BACKGROUND

Implanted electronic medical devices (IEMDs) are electronic devices that are installed inside the body for medical purposes and used for treatment or diagnostic purposes. They are designed to stay in the body for long periods of times. Heart pacemakers, insulin pumps, and neurostimulators are some examples of IEMDs. Many IEMDs are equipped with communication and networking functionalities that allow them to provide sophisticated features such as reporting measurements or alarms in real time or changing their settings or configuration without removing them from the body.

The use of electromagnetic waves to communicate wirelessly with an IEMD makes them vulnerable to many cyber-attacks. The Department of Homeland Security in the United States characterized three vulnerabilities in pacemakers which allowed an attacker to hijack the wireless link and send commands that could harm patients such as performing a shock that is not needed, send streams of wake-up commands to deplete the battery, or eavesdrop on sensory data sent to external Wireless Programmer and Reader (WPR). Any implanted electronic medical device (IEMD) utilizing electromagnetic waves for wireless functionalities is subject to the same vulnerabilities. There is a need for more secure system and method for operating these devices.

SUMMARY

This disclosure generally relates to a Two Factor Authentication using Molecular Communication (TFAMoCo) system and method to prevent hacking the wireless link of an IEMD. A two factor authentication system is provided comprising a transmitter which is configured to release signaling molecules in the body in a controlled manner to modulate information, and a receiver such as an IEMD with molecular communication (MC) module for receiving data by measuring the concentration of molecules in the body to infer the encoded information in addition to an electromagnetic module (EM) to make wireless link with WPR, and a WPR used to reprogram, read logged data, or enable or disable the IEMD, and signaling molecules, and a communication channel which is a human body.

In another aspect of the invention, a Two Factor Authentication using Molecular Communication (TFAMoCo) method is provided, comprising the steps (a) A Personal Identification Number (PIN) is generated either manually or randomly and input into the molecular communication transmitter, (b) The transmitter is connected to the body, (c) The transmitter sends PIN number using molecules by controlling the amount and release time of signaling molecules (d) The IEMD changes to wake up mode after detecting a change in the concentration of signaling molecules and process the transmitted signal and extract the PIN number, (e) The IEMD enables the EM module, (f) The IEMD requests the PIN number via the wireless link from the WPR, (g) The WPR operator input the same PIN generated in step (a), (h) The IEMD compares the PIN values received through the MC module and the one received from the EM module, (i) If the PIN received from MC module equals PIN received from the EM module, the IEMD moves to step (j) otherwise it moves to step (k), (j) The IEMD keeps EM module active and WPR access is granted to the IEMD resources from the wireless link, (k) The IEMD disables the EM module and returns to sleep mode.

Other features will be apparent from the accompanying drawings and from the detailed description that follows.

BRIEF DESCRIPTION OF DRAWINGS

Example embodiments are illustrated by way of example only and not limitation, with reference to the figures of the accompanying drawings, in which like references indicate similar elements and in which.

Other features of the present disclosure will be apparent from the detailed description of embodiments that follows.

DETAILED DESCRIPTION

In this disclosure, we propose a two factor authentication method using molecular communication (TFAMoCo) in conjunction with electromagnetic communication to circumvent the connectivity shortcomings of IEMDs. Molecular communication (MC) uses molecules for conveying information by modulating it using the properties of molecules such as number, type or time of release. The motivation behind using MC in the body mainly lies in the fact that MC links provides privacy and security. The signaling molecules are released in, and confined to, the body fluids which provide high robustness against eavesdropping, particularly when compared to electromagnetic waves. In addition, hijacking the communication link cannot take place without noticeable physical contact with the body which the patient would be aware of in most cases and thus be capable of preventing it. The present invention is described in enabling detail in the following examples, which may represent more than one embodiment of the present invention.

Figure 1:
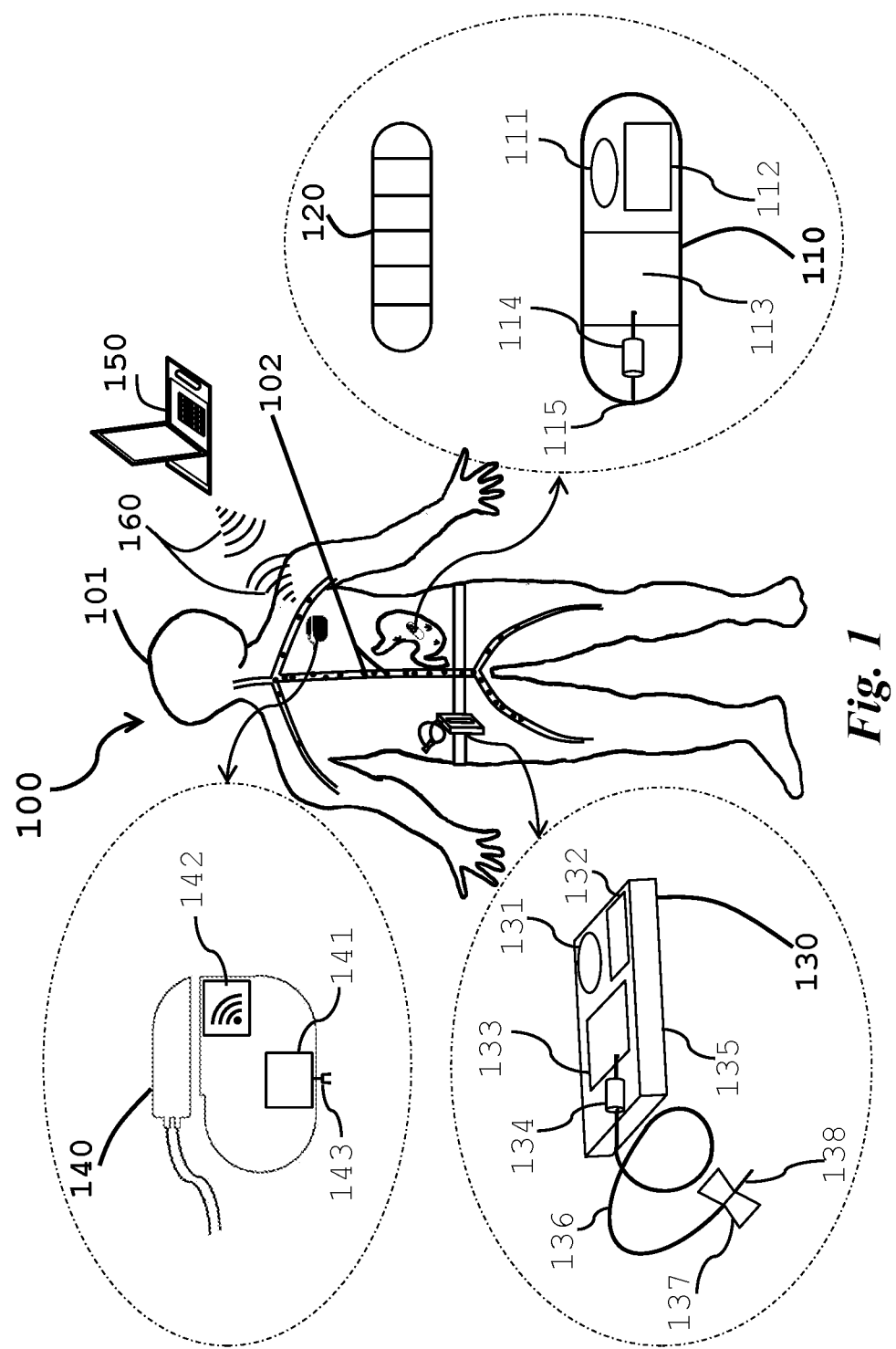
FIG. 1 is a diagram showing one configuration of a system using Two Factor Authentication with Molecular Communication (TFAMoCo) according to an embodiment of the present invention.

FIG. 1 is a diagram showing one configuration of a system using Two Factor Authentication with Molecular Communication (TFAMoCo) according to an embodiment of the present invention. The TFAMoCo system 100 comprises a transmitter or a set of transmitters (110,120,130), signaling molecules 102, an IEMD 140 such as a pacemaker, a wireless programmer and reader (WPR) 150, a human body 101 as a communication channel.

The human body 101 has an IEMD 140 such as a pacemaker in this example but other IEMDs are possible in other embodiments of this invention. The IEMD 140 is implanted to perform specific therapeutic tasks and ideally is equipped with an electromagnetic EM module 142 that has a wireless interface that enables wireless connection 160 with a WPR 150. The WPR 150 can be used to reprogram, read logged data, enable or disable the IEMD 140 without removing it from the patient. In this invention, we propose adding a new MC module 141 that has a molecular interface 143 that can detect the presence or absence of a specific signaling molecules 102 and has a method and mechanism known in the art to estimate their count or concentration in its vicinity.

The signaling molecules 102 can be any substance that can be absorbed, distributed, metabolized, and excreted safely by the human body. In addition, it must be detectable and measurable by the IEMD's MC module 141. The transmitters (110,120,130) release signaling molecules in the human body to communicate with the IEMD's MC module 141. They encode information by controlling the amount and release time of signaling molecules.

There are many routes of administering signaling molecules into the body, such as but not limited to, oral, dermal, intravenous, or inhaling. The route of administration determines the transmitter form. For example, in oral administration the transmitter components can be enclosed in a pill shaped container so that they can be taken orally and work from inside the body such as 110 and 120. Alternatively, the transmitter could be designed to work externally by attaching it to the body from outside such as the transmitter 130.

FIG. 1 (120) shows an example of a passive multi compartment smart pill that can modulate multiple symbols that can be taken orally. Each compartment may contain a solid or liquid form of signaling molecules or combination of both. The compartments may be made from membranes or materials that has different biodegradability or made from the same material with different thickness so that the dissolution time of one compartment is different than the other. By setting different amounts of signaling molecules and changing the dissolution time of each compartment, the pill can control the amount and release time of signaling molecules to encode different symbols.

FIG. 1 (110) shows an active transmitter in the form of a pill that can be taken orally and work from inside the body. The transmitter may comprise a microcontroller 111, power source 112, signaling molecules reservoir 113, a releasing mechanism 114, and an aperture 115. The microcontroller 111 is powered by the power source 112 and is programmed to perform all the functions of a traditional transmitter except that it has a mechanism to control the signaling molecules amount and release time based on the information to be modulated. In this example, the release mechanism could be controlled using a pump 114 that is powered to administer molecules through the aperture 115 and switched off to stop.

FIG. 1 (130) shows an active transmitter that could be placed inside a small box 135 with an infusion set 136 that has a cannula 138. The cannula 138 can be inserted through the skin into the body and fixed in place with a patch 137 while delivering the signaling molecules to the body. The transmitter may comprise a microcontroller 131, power source 132, signaling molecules reservoir 133 and a releasing mechanism 134. The microcontroller 131 is powered by the power source 132 and is programmed to perform all the functions of a traditional transmitter except that it has a mechanism to control the signaling molecules amount and release time based on the information to be modulated. In this example, the release mechanism could be controlled using a pump 134 that is powered to administer molecules and switched off to stop.

Figure 2:
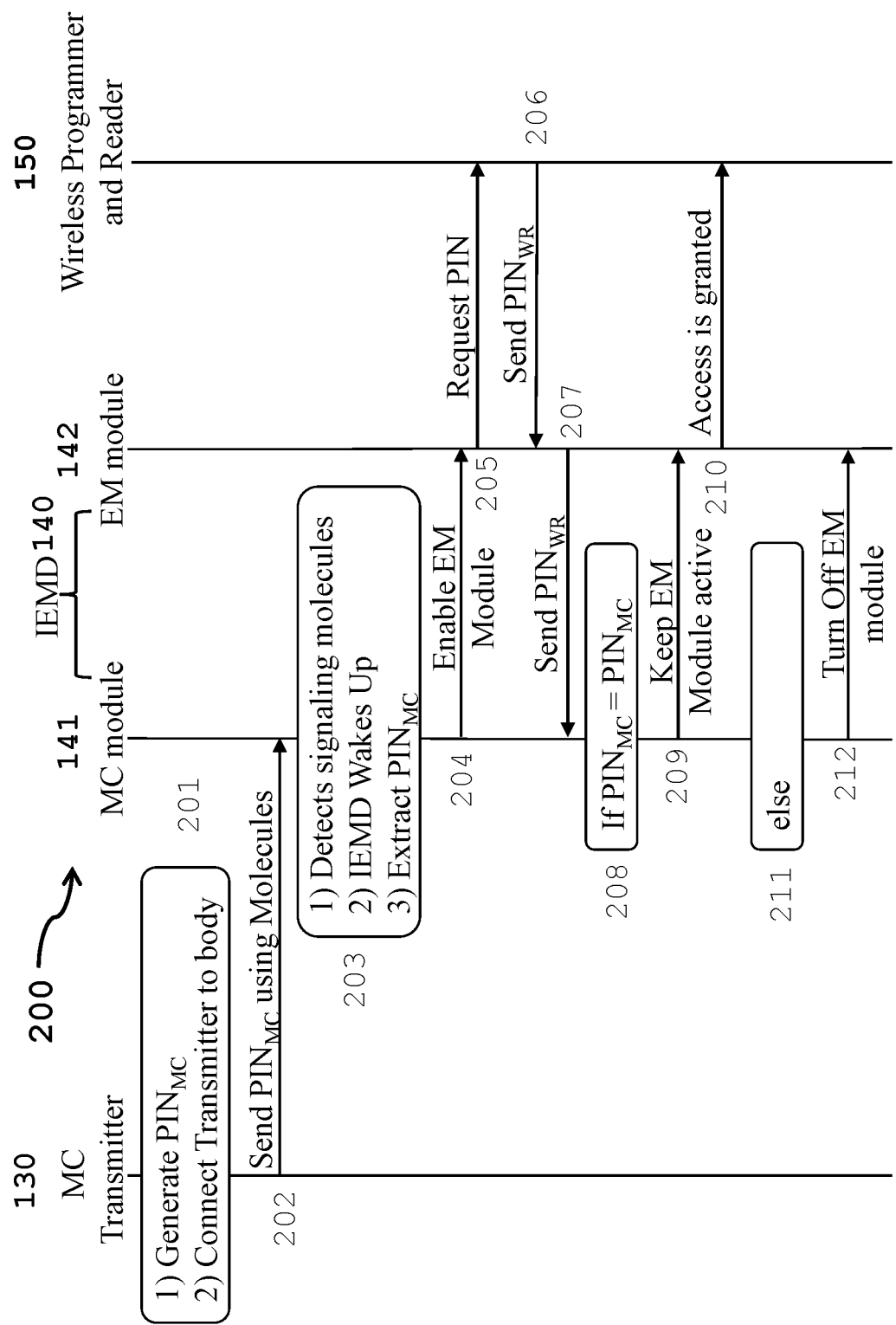
FIG. 2 is a process flow chart illustrating steps of TFAMoCo method according to an embodiment of the present invention.

FIG. 2 is a process flow chart illustrating steps 200 of TFAMoCo method according to an embodiment of the present invention. Ideally, the IEMD 140 is in sleep mode and its EM module 142 is turned off to prevent hacking the device. However, the molecular communication interface 141 is on and measures the concertation of the signaling molecules 102. The TFAMoCo method comprises a set of steps to wake up the IEMD 140 and activate its EM module 142 utilizing the IEMD's MC module 141 for detecting a molecular signal that carries a valid PIN number. The PIN number can be composed of a string of digits, letters, symbols, or combination of them. A PIN can be numeric or alpha-numeric of fixed length. For example, the code 9102 is a 4-digit numeric PIN. At step 201, a $PIN_{MC}$ number is generated either manually or randomly and input into the molecular communication transmitter. In the case of an active transmitter, the $PIN_{MC}$ may be keyed using but not limited to a keypad or any alternative input method known in the art. In the case of a passive transmitter, the $PIN_{MC}$ may be encoded using combinations of signaling molecules and dissolution time of the compartments holding the signaling molecules. After that, the transmitter is connected to the body. In one embodiment, the connection may be realized suing a transmitter such as the one shown in FIG. 1 (130) by connecting the transmitter needle 138 to the body. In another embodiment, the transmitter may be connected by taking it orally such as pill shaped transmitter shown in FIG. 1 (110,120). At step 202, the transmitter starts sending $PIN_{MC}$ number using molecules by controlling the amount and release time of signaling molecules as explained in FIG. 3. At step 203, the IEMD wakes up after detecting the signaling molecules and process the transmitted signal to extract the $PIN_{MC}$ number. At step 204, the IEMD enables the EM module 142 and request the PIN number via the wireless link from the WPR 150 at step 205. At step 206, the WPR 150 operator input the same $PIN_{MC}$ generated in step 201 which is denoted as $PIN_{WR}$ and send it to the EM module 142. At step 207, in one embodiment, the EM module 142 forwards $PIN_{WR}$ to the MC module 141. At step 208, the IEMD MC module 141 compares the PIN values received through the MC module ($PIN_{MC}$) and the one received from the EM module ($PIN_{WR}$). If the $PIN_{MC}$ equals $PIN_{WR}$, the IEMD moves to step 209 and keeps EM module active and grant WPR 150 access to the IEMD resources from the wireless link in step 210. Otherwise, the IEMD moves to step 211 and then disable the EM module at step 212 to prevent an authorized access.

In another embodiment, the comparison between $PIN_{MC}$ equals $PIN_{WR}$ may be done by software or hardware or both or any other method known in the art. In addition, it may be in any module or part of IEMD known in the art such as but not limited to an IEMD's microprocessor.

Figure 3:
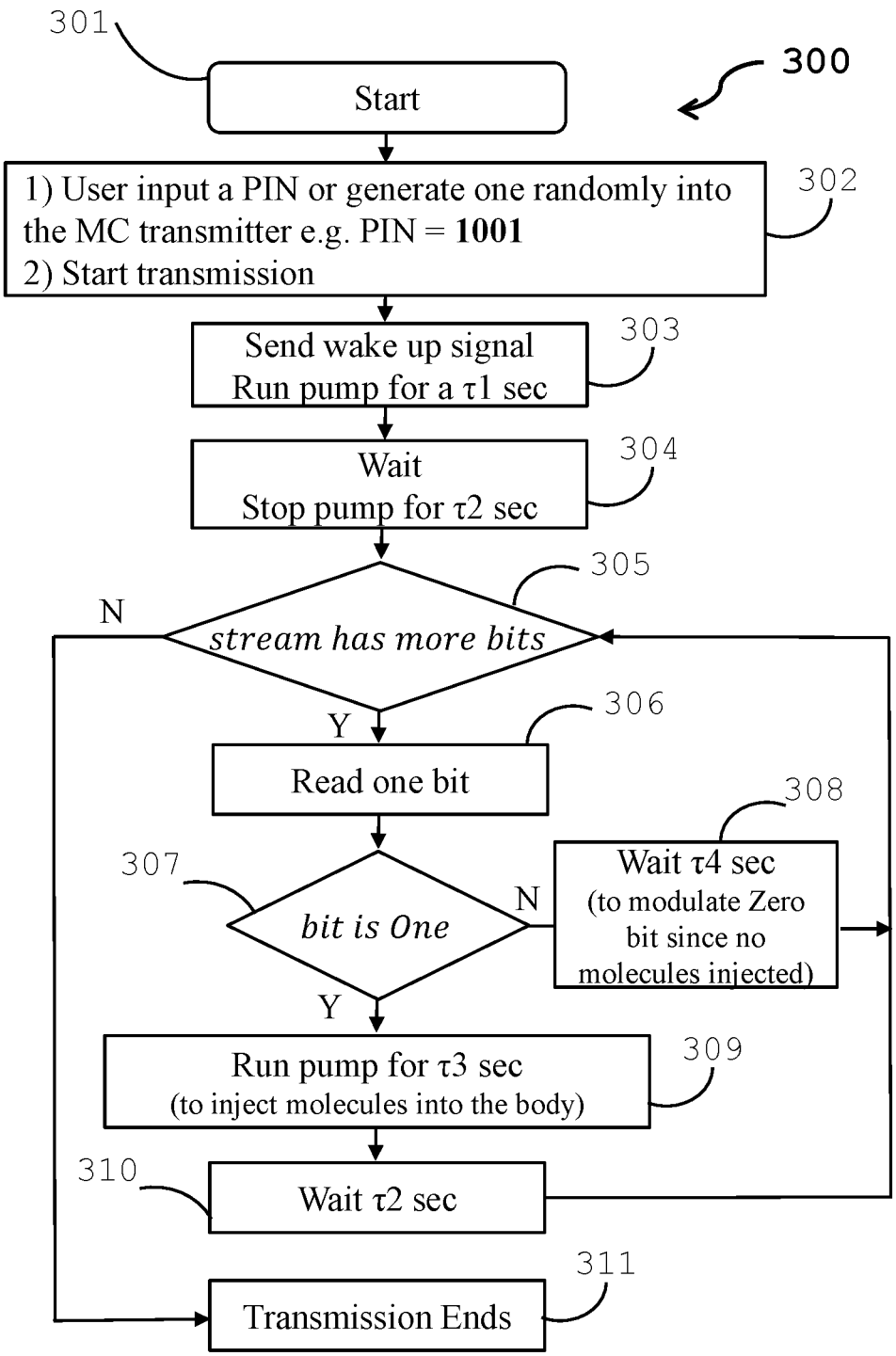
FIG. 3 is a process flow chart illustrating steps of an example implementation of transmitting a PIN number using molecular communication signaling used by a transmitter according to an embodiment of the present invention.

FIG. 3 is a process flow chart illustrating steps 300 of an example implementation of transmitting a PIN number using molecular communication signaling used by a transmitter according to an embodiment of the present invention. The user starts the transmitter at step 301. Then, the user enters a PIN number in the transmitter manually or let the transmitter generate a random pin and start transmission at step 302. In this example, the PIN is composed of four bits such as 1001 but can be longer or shorter. Then, at step 303, the transmitter sends a wake up signal by releasing signaling molecules into the body in this example by running a pump for τ1 seconds that will elevate the concentration of the signaling molecules to a level that can be triggered by the MD module in the IEMD. At step 304, the transmitter stops releasing the signaling molecules for τ2 seconds in this example by stopping the pump to allow the body to absorb, distribute, metabolize, and excrete the signals molecules such their concentration level stays the same or start to decline. Then, the transmitter uses a modulation scheme such as, but not limited to, the on off keying (OOK) to create a molecular signal. The OOK is done by reading a bit at a time at steps 305 and 306. If the bit is one go to step 309 and inject signaling molecules into the body by running a pump for τ1 seconds. At step 310, the transmitter stops injecting signaling molecules, in this example, by means of stopping the pump for τ2 seconds then moves to step 305. On the other hand, if the bit is zero at step 307, the transmitter does not inject signaling molecules to the body, in this example, perform step 308 by keeping the pump off and waits for τ4 seconds before it proceeds to step 305. The process continues till all bits are transmitted where the transmitter moves from step 305 to 311 and ends the transmission. The values for τ1, τ2, τ3, and τ4 are selected based on the ADME process rates so that the receiver can detect molecular signal and infer the sent message. An example of a modulated input signal sent using the OOK is shown in FIG. 4.

Figure 4:
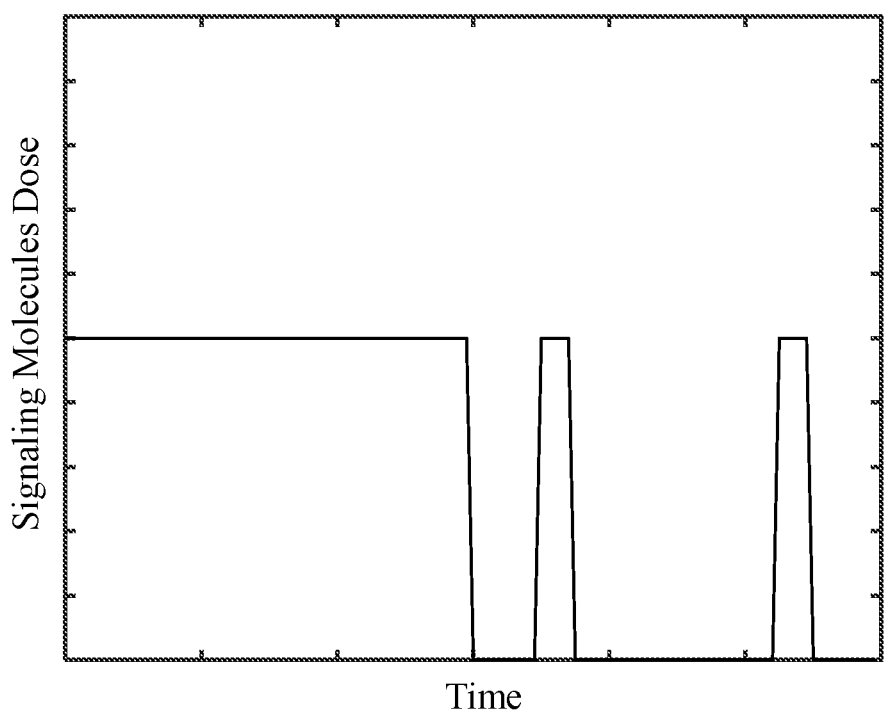
FIG. 4 is a diagram showing an example of an input signal modulating an example PIN number 1001 according to an embodiment of the present invention.

FIG. 4 is a diagram showing an example of an input signal modulating an example PIN number 1001 according to an embodiment of the present invention. In this example, the transmitter is using on off keying where it injects signaling molecules to modulate a one and stop injecting to modulate a zero.

Figure 5:
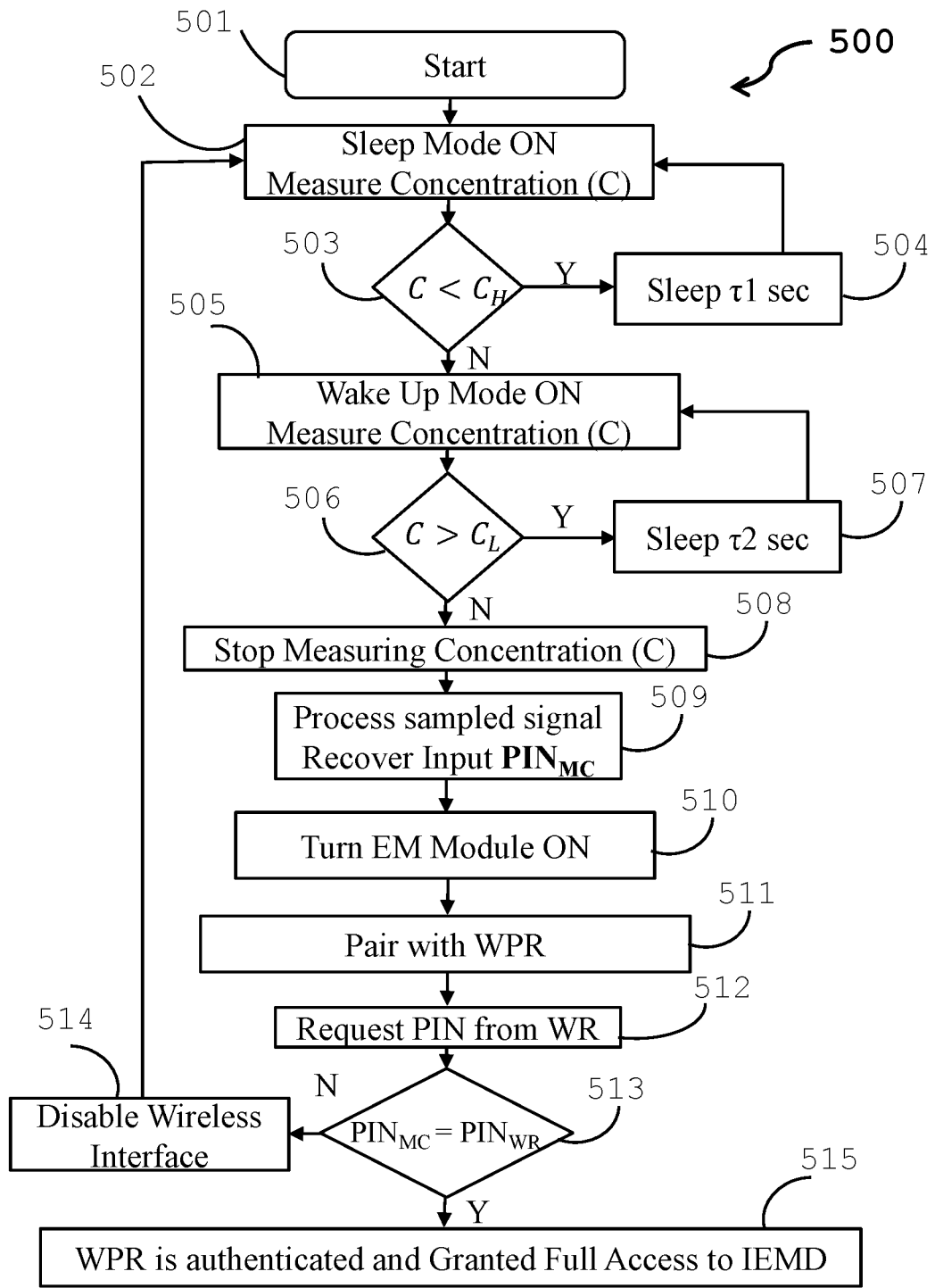
FIG. 5 is a process flow chart illustrating steps of an example implementation of TFAMoCo at an IEMD according to an embodiment of the present invention.

FIG. 5 is a process flow chart illustrating steps 500 of an example implementation of TFAMoCo at an IEMD according to an embodiment of the present invention. At step 501, the operator starts the IEMD. Once the IEMD is started and initialized 501, it stays on and measures the concentration of the signaling molecules while switching between the sleep and wake up modes. The IEMD enters the sleep mode 502 after starting and measures the concentration of the signaling molecules (C). At step 503, it checks if C is less than a predefined concentration level $C_H$, it goes to step 504 and sleeps for τ1 seconds before it returns to step 502 and takes another measurement. However, at step 503, if C is not less than $C_H$, it assumes that the transmitter is transmitting and moves to step 505 where it changes to wake up mode and measure the signaling molecules concertation. At step 506, if C is greater than a predefined concentration level $C_L$, it goes to step 507 and waits for τ2 seconds. Then, it returns to step 505 again and take another measurement of C. Ideally, τ2 should be much smaller than τ1 to enable the MC module to measure more frequently and get more measurements. In this example, the measured concentration values are stored to be processed later to infer the information send by the transmitter. At step 506, if C is not greater than $C_L$, the IEMD assumes that the transmitter has finished transmitting and moves to step 508. An example of the received sampled signal is shown in FIG. 6.

At step 508, the IEMD stops measuring C and moves to step 509. At step 509, the IEMD process sampled signal to retrieve PIN sent by the transmitter. At step 510, the IEMD turns the EM module on and starts pairing with a WPR at step 511. At step 512, the IEMD EM module requests the PWR to provide the PIN number the operator transmitted through the MC module. At step 513, the IEMD compares the value of PIN received from MC module with the value provided by WPR through the EM module. If the WPR provides the correct PIN number, it moves to step 515 where the WPR is authenticated and its access to the IEMD resources is granted. Otherwise, it moves to step 514 and disables the EM module, then, it returns to sleep mode at step 502.

Figure 6:
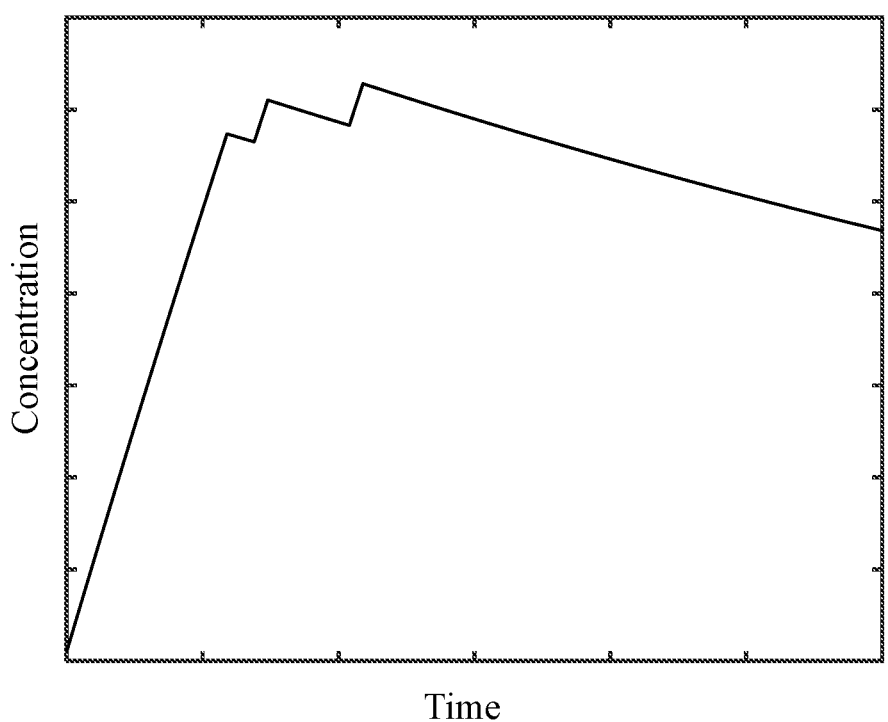
FIG. 6 is a diagram showing an example of sampled molecular signal captured by a MC module in an IEMD according to an embodiment of the present invention.

FIG. 6 is a diagram showing an example of sampled molecular signal captured by a MC module in an IEMD according to an embodiment of the present invention. The diagram shows several concentration peaks. The first peak has a very sharp increase in the concentration level due to the first dose injected by the transmitter to signal for the duration of τ1 seconds to trigger the wake-up mode in the IEMD. After that, a constant decrease in concentration takes place as a result of eliminating the signaling molecules from the body while the transmitter stopped injecting molecules for τ2 seconds. Then, we observe a second peak that results from modulating the first bit where the transmitter keeps injecting molecules for τ3 seconds to modulate a one. Then, there is a decrease in the concentration for duration τ2+2*τ4 seconds which results from transmitters silence after sending a one and for modulating two consecutive zeros by stopping injecting molecules during this time. Finally, we see a third peak which corresponds to modulating the fourth bit which happens to be one. The concentration continues to decrease slowly over time afterwards because the transmitter is not injecting more molecules and the body continues eliminating the remaining molecules from the body.

Figure 7:
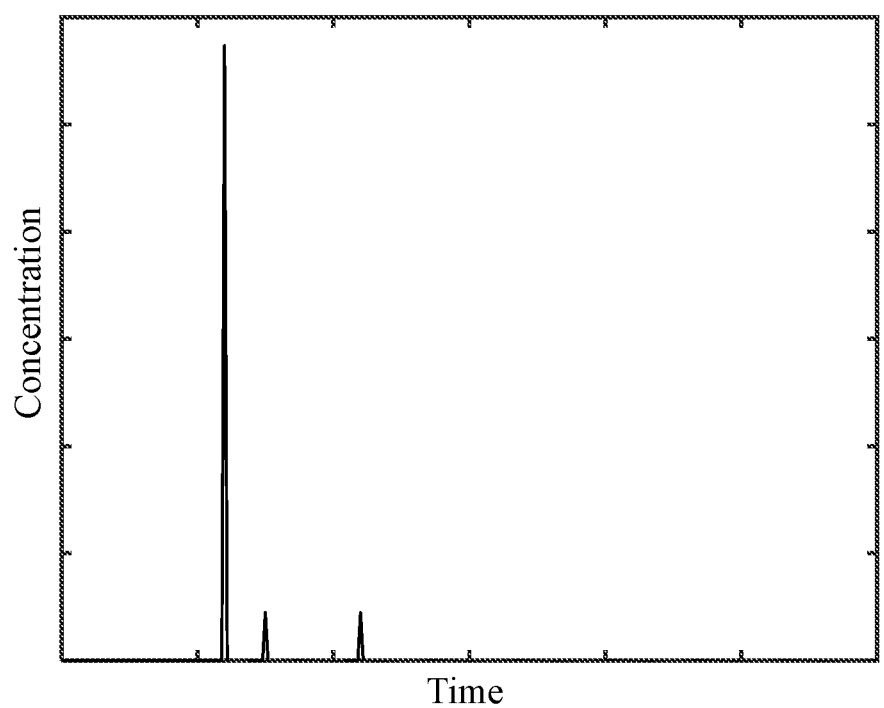
FIG. 7 is a diagram showing an example of a recovered input signal at the IEMD according to an embodiment of the present invention.

FIG. 7 is a diagram showing an example of a recovered input signal at the IEMD according to an embodiment of the present invention. The figure shows 3 spikes. The first represents the wake-up signal. During the first bit duration after the wake-up signal, there is a spike. However, there are no spikes for duration the second and third bits. After that, there is a spike during the duration of the fourth bit. The presence and absence of spikes indicates the location where there are ones and zeros in the transmitted signal.

What is claimed is:

1. A system for two factor authentication using molecular communication to prevent hacking of a wireless link of an implanted electronic device (IEMD), comprising:

a transmitter configured to release signaling molecules in a body to encode an authentication number by controlling the amount and release time of the signaling molecules, the authentication number correlated with information wirelessly transmitted by the wireless link; and a receiver embedded as part of the IEMD, the receiver comprising:

a molecular communication (MC) module for measuring the signaling molecules in the body and decoding the authentication number by measuring a concentration of the received signaling molecules; and an electromagnetic (EM) module to make a wireless link with an external wireless programmer and reader to communicate the decoded authentication number, wherein the wireless programmer and reader is configurable to compare and authenticate the authentication number based on the wirelessly transmitted information and directs the IEMD to be active if the authentication number is authenticated and inactive if the authentication number is not authenticated, and wherein the signaling molecules are absorbed, distributed, metabolized, and excreted by the body, and wherein the system is adapted to use a communication channel comprising the circulatory system in the body as a medium through which the signaling molecules travel from the said transmitter to the said receiver.

2. The system of claim 1, wherein the transmitter is a plurality of transmitters, wherein the receiver is a plurality of receivers.

3. The system of claim 1, wherein the transmitter is internal to the body, and wherein the transmitter is external to the body.

4. The system of claim 1, wherein the transmitter is a passive transmitter that delivers molecular signals without electrically powered parts utilizing physical and chemical properties of the body.

5. The system of claim 1, wherein the transmitter comprises a pill taken orally, the pill comprises a plurality of compartments, each compartment containing the signaling molecules.

6. The system of claim 1, wherein the transmitter comprises a patch, the patch comprises of a plurality of compartments, each compartment containing the signaling molecules.

7. The system of claim 1, wherein the transmitter is an active transmitter that comprises a power source, a reservoir for the signaling molecules, and a releasing mechanism to release the signaling molecules.

8. The system of claim 1, wherein the transmitter comprises a pill taken orally, the pill comprises a microcontroller, a power source, a reservoir for the signaling molecules, a releasing mechanism to release the signaling molecules, and an aperture.

9. The system of claim 8, wherein the releasing mechanism is controlled using a pump.

10. The system of claim 7, where the transmitter is placeable inside a box that comprises an infusion set with a cannula, the cannula is insertable through skin and into the body, the transmitter further comprising a patch to hold the cannula in place while delivering the signaling molecules to the body.

11. The system of claim 1, wherein the transmitter comprises a microcontroller, a power source, a reservoir for the signaling molecules, and a releasing mechanism to release the signaling molecules.

12. The system of claim 11, wherein the releasing mechanism is controlled using a pump.

13. The system of claim 5, wherein each compartment having a dissolution time different than other compartments by either being made from membranes or materials having different biodegradability than other compartments, or being made from a material having a different thickness than other compartments.

14. The system of claim 6, wherein each compartment having a different release time than other compartments by either being made from membranes or materials having different biodegradability than other compartments, or being made from a material having a different thickness or different size apertures than other compartments.

15. The system of claim 14, wherein the signaling molecules are carried from the compartments and injected into the body via micro needles.

* * * * *